United States Patent [19]
Knifton

[11] 3,991,101
[45] Nov. 9, 1976

[54] PROCESS FOR PREPARING UNSATURATED ALIPHATIC ESTERS

[75] Inventor: John F. Knifton, Poughquag, N.Y.

[73] Assignee: Texaco Inc., New York, N.Y.

[22] Filed: June 22, 1973

[21] Appl. No.: 372,899

[52] U.S. Cl. .................. 260/486 AC; 252/437; 260/485 R; 260/487; 260/533 A
[51] Int. Cl.² .......................................... C07C 69/54
[58] Field of Search .................. 260/486 AC, 533 A

[56] References Cited
UNITED STATES PATENTS
3,700,706  10/1972  Butter ........................... 260/497 B
FOREIGN PATENTS OR APPLICATIONS
507,778  6/1939  United Kingdom OTHER PUBLICATIONS
Monomers Edt. by E. R. Blouk p. 3.
Maitlis, P. M., "The Org. Chem. of Palladium" vol. II, Academic Press, N.Y. 1971 pp. 22–27.

*Primary Examiner*—Paul J. Killos
*Attorney, Agent, or Firm*—T. H. Whaley; C. G. Ries; Bernard Marlowe

[57] ABSTRACT

This invention relates to the carbonylation of unsaturated aliphatic halides by the insertion of carbon monoxide into the carbon-halogen bond of said unsaturated aliphatic halide, in the presence of a hydroxylated coreactant, to form an unsaturated, halogen-free, aliphatic ester, using as catalyst homogeneous noble metal complexes with Group VB donor ligands in combination with Group IVB metal halides.

15 Claims, No Drawings

PROCESS FOR PREPARING UNSATURATED ALIPHATIC ESTERS

SUMMARY OF THE INVENTION

This invention concerns a process for preparing unsaturated aliphatic esters of carboxylic acids from the reaction of unsaturated aliphatic halides with carbon monoxide and a hydroxylated co-reactant in the presence of a novel class of homogeneous noble metal catalyst.

More specifically, this invention concerns the carbonylation of unsaturated aliphatic halides, particularly vinyl, allyl and propargyl halides, by the insertion of carbon monoxide into an existing carbon-halogen bond in the presence of an alkanol, to form an unsaturated, halogen-free, aliphatic ester, under relatively mild reaction conditions, using as catalysts homogeneous noble metal complexes with Group VB donor ligands in combination with Group IVB metal halide co-catalysts.

BACKGROUND OF THE INVENTION

Unsaturated esters of aliphatic carboxylic acids, as defined herein, are characterized by the presence of at least one and not more than two ester groups (—COOR, wherein R is an alkyl radical preferably containing up to 6 carbon atoms) and at least one but not more than two unsaturated carbon to carbon bonds (either olefinic or acetylenic or a mixture of each) in the molecule.

The unsaturated esters of aliphatic carboxylic acids can be prepared by a great number of procedures set forth in the technical and patent literature.

Several different processes are used commercially to prepare acrylate esters including the less utilized acrylic acid. More than half of the total acrylates prepared in the U.S. employ acetylene as the starting material. The older processes react acetylene with nickel carbonyl in methyl ethyl ketone in combination with carbon monoxide under pressure. While yields and selectivity are good, nickel carbonyl is a highly toxic material.

A more complex version of the above process is to pre-absorb the acetylene in tetrahydrofuran in the presence of an alcohol and carboxylate with carbon monoxide under pressure in the presence of a nickel salt catalyst including Ni(CO)$_4$.

Other known processes react ketene (H$_2$C=C=O) with formaldehyde to produce Beta-propiolactone, which combines with water or an alcohol in the presence of dehydrating agents to form acrylic acid or the respective ester; or selectively oxidize propylene to acrylic acid and acrolein and further oxidize the acrolein to acrylic acid.

The extensive literature on Reppe-type chemistry* teaches that the carbonylation of unsaturated aliphatic halide may proceed either through addition of carbon monoxide to the carbon-carbon unsaturated bond to give, in the presence of a suitable hydroxylated co-reactant, the corresponding halogenated acid derivative. For example, the synthesis of chlorobutanoate esters from allyl chloride:

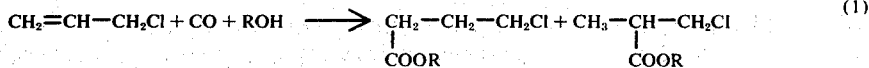
(1)

---
* See "Carbon Monoxide in Organic Synthesis" by J. Falbe, published by Springer-Verlag, N.Y. (1970), Chapter II.

Alternatively, carbon monoxide insertion into the carbon-halogen bond, with halide displacement, may occur, to give, in the presence of the hydroxylated co-reactant such as an alcohol, the corresponding unsaturated acid derivative. For example, the synthesis of vinyl acetate esters from allyl chloride:

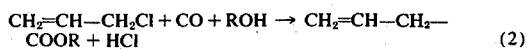
(2)

In the case of the carbonylation of allylic halides, carbonylation via CO insertion into the carbon halogen bond is documented in the literature (British Pat. No. 987,274[1965]). However, carbonylation via CO insertion with the homogeneous ligand-stabilized noble metal catalysts with Group IVB metal halide co-catalysts of this invention provides an improved process for the synthesis of unsaturated, halogen-free, acid derivatives with improved yields and selectivity to the unsaturated, halogen-free, acid derivative as, for example, in the synthesis of vinylacetate esters from allyl chloride.

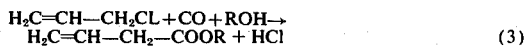
(3)

The carbonylation of vinylic chlorides normally proceeds through Co addition to the carbon-carbon unsaturated bond (cf equation 4) to give the corresponding halogenated acid derivative, for example the synthesis of α-chloropropionate ester from vinyl chloride (German Pat. No. 1,227,023[1966]).

(4)

In this invention, noble metal catalysts, particularly ligand-stabilized noble-metal halide catalysts with Group IVB metal halide co-catalysts, are used to catalyze the insertion of CO into the carbon halogen bond of the vinylic halide to give unsaturated aliphatic, halogen-free, acid derivatives. For example, the synthesis of acrylate esters from vinyl chloride:

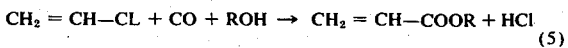
(5)

It should be noted that the instant invention is also distinguishable over previous cases* in that:

1. In the previous cases, while the same classes of homogeneous catalysts are used in conjunction with carbon monoxide and unsaturated substrates, alpha-olefins are the substrates in the previous cases rather than unsaturated aliphatic halides such as vinyl chloride or allyl chloride.

2. In the previous cases only carbon monoxide addition to the unsaturates takes place, whereas in the instant application carbon monoxide insertion into the carbon-halogen bond with displacement of halogen takes place, without addition to the unsaturated bond.

3. In the previous cases only stoichiometric quantities (2 moles) of the Group VB donor ligand, typified by triphenylphosphine, to noble metal component are used in the reaction, whereas excess (1 to 10 moles) of triphenylphosphine to noble metal component may be used in some cases for the carbonylation of unsaturated aliphatic halides.

*U.S. Pat. No. 3,819,669 and U.S. Pat. No. 3,919,217

PROCESS DESCRIPTION

In the broad practice of this invention, unsaturated aliphatic mono-halides are converted to unsaturated aliphatic esters of carboxylic acids in good yield and relatively uncontaminated with halogen-containing by-products by a process of:

a. admixing each mole of at least one unsaturated aliphatic halide to be converted to an unsaturated aliphatic ester, with at least a molar equivalent of hydroxylated co-reactant, in the presence of at least stoichiometric quantities of carbon monoxide, under superatmospheric pressures, in the presence of at least a catalytic amount of a catalyst consisting of a noble metal halide complex selected from the group consisting of platinum and palladium halide complexes, containing one or more Group VB donor ligands, in the presence of a Group IVB metal halide co-catalyst, in the absence of substantial quantities of oxidizing agents and water to form a reaction mixture, and b. heating said pressurized, substantially oxidizer-free water-free reaction mixture at elevated temperatures until conversion of the unsaturated aliphatic halide contained in said reaction mixture to the unsaturated ester takes place, and c. optionally isolating the unsaturated aliphatic esters that are contained therein.

In order to present the inventive concept in the greatest possible detail as to promote its understanding, the following supplementary disclosure is submitted:

A. Process Sequence and Variations. In general, the components of the aforementioned reaction mixture including optional inert solvent, hydroxylated co-reactant, unsaturated aliphatic halide and catalyst may be added in any sequence as long as sufficiently good agitation is provided to assure the formation of a homogeneous mixture. For example, the following represent some variations insofar as the catalyst, sequence of CO and heating that may be made without departing from the inventive process. These modifications include:

1. The catalyst may be preformed and added to the reaction mixture.

2. To minimize stability problems with the homogeneous catalysts, it is preferred to form the catalyst in situ, usually by first adding the Group IVB metal halide in anhydrous form in excess over what is required by stoichiometry, followed by the addition of ligand stabilized noble metal salt such as $PdCl_2[P(C_6H_5)_3]_2$. Optionally the Group VB donor ligand such as triphenylphosphine is also present in excess before the reaction mixture is heated.

3. A third variation is that the catalyst is prepared in situ by adding as separate components of the reaction mixture the noble metal halide, such as palladium (II) chloride, the Group VB donor ligand, such as triphenylphosphine, and the Group IVB metal halide co-catalyst such as tin(II) chloride.

After using variation 1, 2 or 3, the reactor, containing catalyst, agitated deoxygenated inert solvent and hydroxyl-containing co-reactant is sealed, carbon monoxide is added to the agitated system, which is heated to about the reaction temperature and to autogenous pressures. After a homogeneous system is obtained, the unsaturated aliphatic halide, such as vinyl chloride, is added, and the pressure is raised until the desired psig is obtained. At the end of a sufficient reaction time, either empirically determined beforehand or determined by monitoring samples withdrawn for analysis during the reaction, the reaction is terminated, cooled, vented and worked up.

4. A substantial process variation that can be employed when the catalyst is formed in situ in an inert solvent is to heat the catalyst containing solution to temperature under an inert atmosphere or a slightly elevated pressure of CO, and then to add the hydroxylated co-reactant, the unsaturated aliphatic halide and carbon monoxide with efficient agitation and to maintain the CO pressure in the reactor until the ester is formed.

B. Homogeneous Noble Metal Catalyst — The homogeneous noble metal catalyst of this invention normally consists of at least three components, a noble metal halide, selected from the group consisting essentially of platinum and palladium halides, complexed with one or more Group VB donor ligands, and in combination with a Group IVB metal halide co-catalyst.

Each Group VB donor ligand contains one or more donor atoms selected from Group VB of the Periodic Chart of the Elements (Advanced Inorganic Chemistry by F. A. Cotton and G. Wilkinson, 2nd Ed., 1966), preferably it contains one or more trivalent phosphorus or arsenic atoms. One class of such ligands may be defined by the general formula:

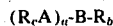

$(R_cA)_a-B-R_b$ wherein B represents the element from Group VB, R represents hydrogen atoms, aryl, alkyl, or mixed alkyl aryl groups, which may contain less than 20 carbon atoms and need not be the same, A may represnt oxygen, nitrogen or sulfur, or materials thereof, $a$ has a value of 0 to 3, $b$ has a value of 3-$a$, and $c$ is equal to 1 or 2. It is also suitable for the organic radical R to contain functional groups, to be substituted with alkyl, alkoxy, halogen and other substituents, and to satisfy more than one of the valences of the Group V atom, thereby forming a heterocyclic compound with the Group VB atom.

A second type of suitable ligand containing Group V donor atoms is one which is composed of two such Group VB atoms linked by organic radicals. This type of compound is called a bidentate ligand.*

*Defined in Modern Coordination Chemistry, by J. Lewis & R. G. Wilkins, Chap. I, 1st Ed. (1960) Interscience.

Illustrative of suitable Group VB donor ligands which may be used in combination with the noble metal halide and the Group IVB metal halide to form active carbonylation catalysts for the preparation of unsaturated aliphatic esters are:
$P(C_6H_5)_3$, $As(C_6H_5)_3$, $P(CH_3)_2(C_6H_5)$, $P(p-CH_3.C_6H_4)_3$, $P(p-Cl\ C_6H_4)_3$, $P(o-CH_3O.C_6H_4)_3$, $P(p-CH_3O.C_6H_4)_3$, $P(OC_6H_5)_3$, $P(C_6H_{11})_3$, $As(n-C_4H_9)_3$, $P[(p-CH_3.C_6H_4)(C_6H_5)_2]$, $(C_6H_5)_2P(CH_2)_2P(C_6H_5)_2$, $(C_6H_5)_2P(CH_2)P(C_6H_5)_2$ and $Sb(C_6H_5)_3$.

The Group IVB metal halides that may be used as co-catalysts in this invention include the halides of tin(II), tin(IV) and germanium(II). Illustrative examples include tin(II) chloride, tin(IV) chloride, tin(II) bromide and germanium(II) chloride. In certain cases, the anhydrous chlorides of the Group IVB metal halides are favored, with anhydrous tin(II) chloride being the preferred co-catalyst.

The following complexes are among the many ligand-stabilized palladium(II)-Group IVB metal halide complexes and ligand-stabilized platinum(II)-Group IVB metal halide complexes which can be used in the catalytic carbonylation of unsaturated aliphatic halides to unsaturated aliphatic esters:
$PdCl_2[P(C_6H_5)_3]_2$-$SnCl_2$, $PdCl_2[As(C_6H_5)_3]_2$-$SnCl_2$, $PdCl_2[P(OC_6H_5)_3]_2$-$SnCl_2$, $PdCl_2[P(pCH_3O.C_6H_4)_3]_2$-$SnCl_2$, $PdCl_2[P(C_6H_5)_3]_2$-$GeCl_2$, $PdCl_2[P(p-Cl.C_6H_4)_3]_2$-$SnCl_2$, $PtCl_2[P(C_6H_5)_3]_2$-$SnCl_2$, $PtCl_2[As(C_6H_5)_3]_2$-$SnCl_2$ and $PdCl_2[P(C_6H_{11})_3]_2$-$Sncl_2$.

In certain cases the Group VB donor ligand, typified by triphenylphosphine, is used in excess of the amount required for complex formation, and the Group IVB metal halide co-catalyst also in excess in order to obtain a stable and active catalyst. In some cases, particularly in the case of the vinylic halides, this will result in an increased yield of the desired unsaturated aliphatic ester product.

C. Ratio of Noble Metal Catalyst to Unsaturated Aliphatic Halide Substrate — Experimental work indicates that a molar ratio of up to 500 moles of substrates per mole of palladium(II) catalyst complex can be employed in most instances where unsaturated aliphatic halides typified by vinyl halides are used as the substrate. This molar ratio constitutes what is referred to as a catalytic amount. Much lower ratios (i.e. 25 moles of halide substrate per mole of platinum halide) are not harmful but are economically unattractive. For this reason the preferred molar range arrived at in Table III ranges from 50 to 200 moles of substrate per mole of noble metal catalyst.

D. Temperature required for Ester Formation — The temperature range which can be employed for ester formation is variable dependent upon other experimental factors including the substrate employed, the pressure, the concentration and the particular choice of catalyst among other things. Again using vinyl chloride as a typical unsaturated halide and $PdCl_2$-$[P(C_6H_5)_3]_2$-$SnCl_2$ as a representative catalyst, the range of operability is from about 20° to 120° C when superatmospheric pressures of 1000–2000 psig or higher are employed. A narrower range of 80° to 120° C represents the preferred temperature range when the aforementioned vinyl chloride is carbonylated at 2000 psig using the catalyst system described supra. Table II is evidenciary of how this narrower range is derived.

E. Pressure — Superatmospheric pressures of 100 psig to at least 3000 psig lead to substantial conversion of the unsaturated halide to the carboxylic acid (or ester) at temperatures of 20° to 120° C using $PdCl_2[P(C_6H_5)_3]_2$—$SnCl_2$ as catalyst and vinyl chloride or allyl chloride as the unsaturated halide. Tables II and V provide the supporting experimental data.

F. Reaction Times Required — As previously indicated in the analogous discussion on temperatures and pressures required in the reaction, experimental variables are important in arriving at reaction times. Generally substantial conversions (70% or higher) of the substrates to the unsaturated ester can almost always be accomplished within 20 hours with 4 to 6 hours representing the more usual reaction time interval.

G. Unsaturated Aliphatic Monohalides — As used throughout this disclosure, this term refers to three related classes of unsaturated aliphatic halide substrates, wherein the unsaturation (double or triple bonds) in the substrate is only between carbon to carbon atoms. Illustrative of the three classes of unsaturated alkyl halide substrates are those having the groupings:

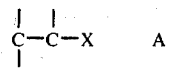   A

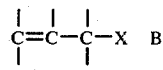   B and

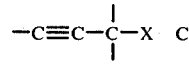   C where X is a halogen atom, and the carbon atom valences indicated are satisfied by hydrogen or alkyl groups. All three categories of unsaturated aliphatic halides and their homologues and analogues lend themselves to conversion to unsaturated esters of carboxylic acids.

Unsaturated allyl halides of structure A are commonly known as vinylic halides, and examples include vinyl chloride, vinyl bromide, vinyl iodide, 1-chloropropene and 2-chloro-2-butene.

Unsaturated alkyl halides of structure B are commonly known as allylic halides. Examples include allyl chloride, allyl bromide, 3-chloro-1-butene and crotyl chloride.

Unsaturated alkyl halides of structure C include acetylenic halides such as propargyl chloride.

J. Hydroxylated Co-Reactant — If it is desired to prepare the unsaturated aliphatic ester products, an alcohol co-reactant must be present in the reaction mixture with the unsaturated aliphatic halide substrate, carbon monoxide and catalyst. The alcohol may be a monohydric primary or secondary alkanol of up to twelve carbon atoms, a substituted alcohol, a phenol, or a substituted phenol. Suitable examples include methanol, ethanol, isopropanol, dodecanol, phenol, 2-chloroethanol, 2-ethylhexanol, methylcyclohexanol and the like.

Alternatively, the alcohol may be a polyol containing two or more hydroxyl groupings. Illustrative examples of suitable polyols include propylene glycol, neopentyl glycol, trimethylol propane and pentaerythritol.

J. Carbon Monoxide Environment — Insofar as can be determined, the best selectivities and conversions of unsaturated aliphatic halide to unsaturated aliphatic ester can be obtained within a reasonable reaction time by using a substantially carbon monoxide gaseous atmosphere. However, particularly in continuous operation the carbon monoxide may be used in conjunction with from about 0 to 30% by volume of one or more inert gases such as nitrogen, argon, neon and the like without experiencing a substantial decrease in yield and selectivity.

K. Inert Solvents — The novel reaction is run most conveniently in the presence of an inert diluent. A variety of solvents can be used, including aromatics such as benzene, toluene and xylenes, halogenated aromatics including o-dichlorobenzene and chloronaphthalene, ethers such as dimethoxyethane and p-dioxane, and halogenated paraffins including methylene chloride. Ketones such as acetone, methyl ethyl ketone and methyl isopropyl ketone may interfere with the reaction in certain cases.

L. Selectivity as defined herein is the efficiency in catalyzing a desired carbonylation reaction with concurrent halide displacement relative to other undesired competing reactions; in this instance carbonylation to the unsaturated aliphatic ester derivative is the desired conversion. Selectivity is usually expressed as a percentile, and is calculated herein by determining the amount of carbonylated product formed, divided by the total amount of carbonylated products which can theoretically form, and multiplying the quotient obtained by 100.

M. Conversion as defined herein is the efficiency in converting the unsaturated halide to non-halogenated unsaturated aliphatic ester products. Conversion is also expressed as a percentile and is calculated herein by dividing the amount of unsaturated halide consumed during carbonylation* by the amount of unsaturated aliphatic monohalide originally charged to the reactor and multiplying the quotient by 100.

*Carbonylation as used throughout this disclosure refers to the absorption of carbon monoxide into the substrate. In the inventive process carbon monoxide absorption is accompanied by halide displacement.

N. By-Products — As far as can be determined, without limiting the invention or its novelty, the essence of the inventive process is carbonylation (carbon monoxide absorption) into the unsaturated halide substrate, accompanied by halide displacement from said unsaturated aliphatic halide substrates. These reactions are catalyzed by the homogeneous noble metal catalysts of this invention. Quantitatively speaking, there are only relatively minor amounts of by-products (less than 20% by weight) of the total product content. Qualitatively speaking the type of by-products varies according to which of the three classes of substrates are being carbonylated.

For example, in the case of the vinyl halides such as vinyl chloride, where methyl alcohol is the hydroxylated co-reactant and bis(triphenylphosphine)palladium(II)-tin(II) chloride is the catalyst employed, some methyl α(alpha)-chloropropionate and methyl propionate are produced, as well as traces of dicarboxylate esters such as dimethyl α-methylmalonate.

In those instances where allylic halides such as allyl chloride are reacted with carbon monoxide and methanol with the same palladium catalyst disclosed supra, again by-products constitute only a small portion of total product. In the instant reaction, no evidence of methyl chlorobutyrates has been found, but small quantities of dicarboxylate esters such as dimethyl α-methylsuccinate and dimethyl glutyrate, and negligible quantities of methyl crotonate have been found. However, when excess triphenylphosphine is added (as is done to obtain overall improvements in the carbonylation process where vinyl halides are used as substrates as shown in Example I), additional carbonylation takes place to such an extent that dicarboxylate esters, such as dimethyl pentanoates, become the major product. Table V is evidenciary of this effect of using excess triphenylphosphine in the case of allylic halides.

Having disclosed the generic and sub-generic aspects of the novel carbonylation process in some detail, it only remains to exemplify various preparations that utilize the three groups of related halide substrates and the homogeneous catalysts used in their carbonylation. These preparations are disclosed in the order of:

1. Vinyl halides
2. Allyl halides, and
3. Propargyl-type halides

Unless otherwise stated, all parts are by weight, all temperatures in degrees centigrade and all pressures in pounds per square inch gauge (psig).

EXAMPLE 1

The preparation of methyl acrylate from vinyl chloride using bis(triphenylphosphine)palladium(II)-tin(II) chloride-triphenylphosphine as catalyst.

PART A

To a glass-lined reactor provided with stirring, heating, cooling and pressurizing means, charged with a stirred deoxygenated mixture of benzene (66 parts by weight) and methanol (12 parts by weight) is added under a nitrogen purge, anhydrous stannous chloride (1.88 parts by weight, 10 mmole), followed by 0.70 parts by weight of bis (triphenylphosphine)palladium-(II) chloride complex* (1.0 mmole) and 1.31 parts by weight of triphenylphosphine (5.0 mmole). Stirring of the light yellow solution is continued for an additional 5–10 minutes at which time the autoclave is sealed, purged with nitrogen and carbon monoxide, and heated to 95° C under 100 psig of carbon monoxide for about 15 minutes. At the end of this time 3.1 parts by weight of vinyl chloride (5.0 mmole) is added to the pressurized reactor and the carbon monoxide pressure raised to 2000 psig. Periodically aliquots are removed for gas chromatographic (g.c.) analysis and after 7 hours, the reactor is cooled down, vented to reduce pressure and the 75 parts by weight of clear liquid recovered and analyzed by g.c. Basis the vinyl chloride charged, a yield of 83 mole % of methyl acrylate is obtained. The remainder of the product is found to be unreacted methanol, vinyl chloride plus some methyl α-chloropropionate.

*Prepared by the method of H. Itatani and J. C. Bailar, J. Amer. Oil Chem. Soc. 44 147 (1967)

PART B

In a run almost identical to that of Part A, the process is repeated using the same proportions of reactants and reaction parameters, except that no stannous chloride is present in the reaction mixture. That is, the uncomplexed bis(triphenylphosphine)palladium(II) chloride is used as the catalyst in the absence of stannous chloride co-catalyst employed in Part A. Analysis of the reaction mixture indicates that, in the absence of stannous chloride, the major reaction is CO addition to the carbon-carbon double bond and that the major product by far is methyl α-chloropropionate (selectivity %-74), with approximately one quarter (¼) as much of the desired methyl acrylate being formed (selectivity %-18) plus a significant quantity of dimethyl α-methyl malonate (selectivity %-8).

PART C

Again the run of Part A is substantially repeated insofar as reaction conditions and reactants are concerned, except that while anhydrous stannous chloride and bis(triphenylphosphine)palladium(II) chloride complex are present, the excess triphenylphosphine is absent from the catalyst system. Again the desired carbonylation with chloride displacement does take place, but vinyl chloride conversion is low, and the total yield of methyl acrylate is only 24 mole %.

The three runs (A to C) appear to document the need for both a Group IVB complexing agent (as illustrated here by stannous chloride) and excess stabilizing ligand (as illustrated by triphenylphosphine) to be present with the palladium(II) in order to obtain good yields of desired methyl acrylate from vinyl chloride.

EXAMPLE 2

Preparation of Methyl Acrylate From Vinyl Chloride Using Homogeneous Platinum Catalysts Using the procedure, equipment, proportions and reaction parameters employed in Example 1, Part A, $PtCl_2(PPh_3)_2$-10.$SnCl_2$ is substituted for the homogeneous palladium complex of Part A on a mole per mole basis. At the end of the reaction time the pressurized reactor is cooled, vented and analyzed using chromatography. Only trace amounts of methyl acrylate could be detected.

A similar result is obtained with the complex $PtCl_2(AsPh_3)_2$-10.$SnCl_2$.

The two runs appear to document that the platinum complexes $PtCl_2(PPh_3)_2$-$SnCl_2$ and $PtCl_2(AsPh_3)_2$-$SnCl_2$ are less effective in producing alkyl acrylates from vinyl chloride than the palladium catalyst of Example 1.

EXAMPLES 3 to 9

Preparation of Methyl Acrylate From Vinyl Chloride With Various Other Homogeneous Palladium Catalyst Compositions Table I, which follows, shows the data obtained when the designated homogeneous ligand-stabilized palladium (II)-Group IVB metal halides are employed as carbonylation catalysts for the subject reaction. For each catalyst composition the Pd:Sn:P molar ratio is held at 1:10:7. The preparative procedure is that described in Example 1, Part A.

TABLE I

| Example | Catalyst Composition | Methyl Acrylate Detected |
|---|---|---|
| 3 | $PdCl_2$—$SnCl_2$—[(p-$CH_3O$ . $C_6H_4$)P] | Yes |
| 4 | $PdCl_2$—$SnCl_2$—[(p-Cl . $C_6H_4$)$_3$P] | Yes |
| 5 | $PdCl_2$—$SnCl_2$—[($CH_3$)$_2C_6H_5$P] | Yes |
| 6 | $PdCl_2$—$SnCl_2$—[($C_6H_{11}$)$_3$P] | Yes |
| 7 | $PdCl_2$—$SnCl_2$—[($C_6H_5$)$_2$(p-$CH_3$ . $C_6H_4$)P] | Yes |
| 8 | $PdCl_2$—$GeCl_2$—[($C_6H_5$)$_3$P] | Yes |
| 9 | $PdCl_2$—$SnCl_2$—[($C_6H_5$)$_3$As] | Trace |

EXAMPLES 10 to 16

Preparation of Methyl Acrylate — Effect of Temperature and Pressure Variations

Table II, which follows, shows data obtained when the $PdCl_2(PPh_3)_2$-10$SnCl_2$-5$PPh_3$ catalyst system is employed for the synthesis of methyl acrylate from vinyl chloride using the procedure set forth in Example 1, Part A, but with the designated conditions of temperature and pressure.

TABLE II

| EXAMPLE | REACTION TEMP.(° C) | PRESSURE (PSIG) | MAXIMUM RATE OF METHYL ACRYLATE FORMATION(M/HR.) | METHYL ACRYLATE SELECTIVITY (MOLE %) |
|---|---|---|---|---|
| 10 | 20 | 1000 | <0.01 | >50 |
| 11 | 80 | 2000 | 0.055 | 79 |
| 12 | 95 | " | 0.094 | 78 |
| 13 | 105 | " | 0.17 | 68 |
| 14 | 120 | " | 0.080 | 90 |
| 15 | 105 | 500 | 0.048 | 70 |
| 16 | " | 100 | 0.032 | >50 |

EXAMPLES 17 to 20

Preparation of Methyl Acrylate — Effect of Vinyl Chloride and Palladium Catalyst Concentrations Table III, which follows, shows data obtained when the $PdCl_2(PPh_3)_2$-10$SnCl_2$-5$PPh_3$ catalyst system is employed for the synthesis of methyl acrylate from vinyl chloride using the procedure set forth in Example 1, Part A, but with the designated concentrations of vinyl chloride and palladium catalyst.

TABLE III

| EX. | [VINYL CHLORIDE], (M) | [Pd], (M) | METHYL ACRYLATE SELECTIVITY (MOLE %) | METHYL ACRYLATE YIELD (MOLE %) |
|---|---|---|---|---|
| 17 | 2.10 | $4.2 \times 10^{-2}$ | 90 | 26 |
| 18 | 0.55 | $1.1 \times 10^{-2}$ | 80 | 84 |
| 19 | 0.60 | $6.0 \times 10^{-3}$ | 68 | 46 |
| 20 | 1.20 | $6.0 \times 10^{-3}$ | 71 | 16 |

EXAMPLES 21 to 25

Preparation of Acrylate Esters From Vinyl Chloride — Effect of Solvents Employed Table IV, which follows, shows the data obtained when various acrylate esters are prepared from vinyl chloride in the designated solvents. The carbonylations are carried out using the procedure and reaction conditions of Example 1, Part A.

TABLE IV

| EXAMPLE | ALCOHOL | SOLVENT | MAJOR CARBOXYLATED PRODUCTS | | |
|---|---|---|---|---|---|
| | | | IDENTITY | SELECTIVITY (MOLE %) | YIELD (MOLE %) |
| 21 | Methanol | m-Xylene | Methyl Acrylate | 78 | 65 |
| 22 | " | o-Dichlorobenzene | " | 82 | 47 |
| 23 | " | p-Dioxane | " | 89 | 40 |
| 24 | Ethanol | 1-Chloronaphthalene | Ethyl Acrylate | 92 | 28 |
| 25 | 2-Ethylhexanol | Benzene | 2-Ethylhexyl Acrylate | 95 | 14 |

EXAMPLES 26 to 28

Carbonylation of Vinyl Halides Catalyzed by Palladium Complexes — Effect of Vinyl Halide Employed Using the procedure, proportions, reaction parameters and palladium catalyst of Example 1, Part A, the following vinyl halides are carbonylated to their corresponding unsaturated acid esters:
1. vinyl bromide
2. 1-chloropropene
3. 2-chloro-2-butene

EXAMPLE 29

The Preparation of Methyl Vinylacetate From Allyl Chloride Using Bis(triphenylphosphine) Palladium(II-Tin(II) Chloride as Catalyst To a glass-lined reactor provided with stirring, heating, cooling and pressurizing means is added 66 parts by weight of benzene and 12 parts by weight of methanol. The solution is deoxygenated with nitrogen, and 1.12 parts by weight of stannous chloride dihydrate (5.0 mmole), 0.35 parts by weight of bis(triphenylphosphine)palladium(II) chloride (0.5 mmole), and 3.82 parts by weight of allyl chloride (50 mmole) are added with stirring. Stirring is continued for 5–10 minutes at which time the solution is reddish in color. The autoclave is sealed, purged with nitrogen and carbon monoxide, and heated to 80° C under 3000 psig of carbon monoxide. After 6 hours at temperature, the reactor is allowed to cool, vented to reduce pressure, and 79 parts by weight of clear liquid recovered and analyzed by g.c.

Basis the allyl chloride charged, the yield of methyl vinylacetate is estimated at 75 mole %. The remainder of the carbonylated product is dimethyl α-methyl-succinate (yield 6.0%) and dimethyl glutyrate (yield 2.8%).

EXAMPLES 30 to 35

Preparation of Methyl Vinylacetate From Allyl Chloride Using Various Palladium and Platinum Complexes Table V, which follows, shows the data obtained when allyl chloride is carbonylated using the designated palladium and platinum catalysts in aromatic or oxygenated solvents according to the procedure of Example 29. Here it should be noted that:

1. Both platinum and palladium complexes are suitable catalysts for the synthesis of methyl vinylacetate from allyl chloride.
2. The addition of excess triphenylphosphine in Example 33 results in lower yields of methyl vinylacetate, and significantly increased yields of the saturated, dimethyl pentanoate esters.

TABLE V

| EXAMPLE | CATALYST | SOLVENT | ALLYL CHLORIDE CONV. (%) | MAJOR CARBOXYLATED PRODUCTS | |
|---|---|---|---|---|---|
| | | | | IDENTITY | YIELD (MOLE %) |
| 30 | $PdCl_2(PPh_3)_2$—$10SnC_2 \cdot 2H_2O$ | Methyl Isobutyl Ketone | 80 | Methyl Vinylacetate | 73 |
| 31 | " | Methyl Ethyl Ketone | 95 | " | 60 |
| 32 | " | Benzene | 99 | " | 75 |
| 33 | $PdCl_2(PPh_3)_2$—$10SnCl_2 \cdot 2H_2O$ 5$PPh_3$ | " | >95 | (Dimethyl Pentanoates[1] (Methyl Vinylacetate | 68 34 |
| 34 | $PdCl_2(AsPh_3)_2$—$10SnCl_2$ | " | >95 | Methyl Vinylacetate | 51 |
| 35 | $PtCl_2(AsPh_3)_2$—$10SnCl_2 \cdot 2H_2O$ | " | 44 | " | Trace |

[1]mixture of dimethyl α-methylsuccinate and dimethyl glutyrate in a 2:1 mole ratio

EXAMPLE 37

The Carbonylation of Propargyl Chloride

Using the procedure described in Example 29, a deoxygenated solution of 66 parts by weight of benzene, 12 parts by weight of methanol, 0.96 parts by weight of stannous chloride (5.0 mmole), 0.35 parts by weight of bis(triphenyl-phosphine) palladium(II) chloride (0.5 mmole), 0.65 parts by weight of triphenylphosphine and 3.73 parts by weight of propargyl chloride is charged to the glass-lined autoclave pressure reactor. The reactor is sealed, purged with nitrogen and carbon monoxide, and the solution stirred at 20° C under 1000 psig of carbon monoxide. After 3 hours, the reactor is vented, and the clear-reddish-brown liquid analyzed. The formation of methyl butynoate is confirmed by g.c. I.R. and NMR measurements.

As the numerous examples and preceding discussion have documented, numerous advantages accrue from the practice of this invention both in its compositional aspect and its process aspects.

For example, a relatively large group of ligand stabilized noble metal (II)-Group IVB metal halide catalysts are provided which were heretofore not known to be useful as catalysts for the conversion of unsaturated aliphatic monohalides to their unsaturated, aliphatic halide-free esters of carboxylic acids. These catalytic compositions offer the further advantage of being readily available by well known preparative procedures, and they have conversion efficacies even at substrate to catalyst molar ratios as high as 200 to 1 molar ratios, dependent upon the unsaturated aliphatic halide substrate, and the particular catalyst employed. Quite unexpectedly, the activity pattern of some palladium complexes does not necessarily follow that of the corresponding platinum complex. This can be seen by the data presented in Examples 1 and 2 and Tables I and V.

Even more surprising is that, as far as is known in the closest art, palladium salt catalysts carboxylate vinyl halide substrates (such as vinyl chlorides) to the α (alpha) halo esters Thus only carbon monoxide addition to the double bond takes place, to the substantial exclusion of halide displacement. To reiterate carbon monoxide insertion with halide evolution (or displacement) is the predominant reaction in applicant's claimed process, and not carbon monoxide addition to the double bond.

In its process aspect this invention provides a novel process for preparing unsaturated aliphatic, halide-free esters of carboxylic acids, particularly acrylate esters and vinylacetate esters. In addition, reaction times are rapid, the process lends itself to either batch or continuous operation, employing standard equipment. Further, conversions of unsaturated halides are ordinarily above 70% and selectivities to the unsaturated esters are of the order of 80% and higher.

A further advantage of the instant invention is that while in some respects reaction conditions are critical to success, in other respects the process offers flexibility. That is, numerous modifications and changes can be made in the choice of catalyst and unsaturated halide substrate, without departing from the inventive concept. The metes and bounds can best be determined by reading the claims which follow in light of the preceding specification.

What is claimed is:

1. A process for converting unsaturated aliphatic vinylic monohalides to alpha-unsaturated aliphatic esters of carboxylic acids in good yield and relatively uncontaminated with halogen-containing by-products by a process of:
   a. admixing each mole of unsaturated aliphatic vinylic monohalide to be converted to said alpha unsaturated, aliphatic ester, with at least a catalytic amount of a homogeneous palladium catalyst consisting of at least three components, a palladium halide, complexed with at least a stoichiometric quantity of a Group VB donor ligand, and in combination with a Group IVB metal halide co-catalyst, said catalyst being selected from the group consisting of:
   $PdCl_2$-$SnCl_2$-$[(p-CH_3O.C_6H_4)P]$
   $PdCl_2$-$SnCl_2$-$[(p-Cl.C_6H_4)_3P]$
   $PdCl_2$-$SnCl_2$-$[(CH_3)_2C_6H_5P]$
   $PdCl_2$-$SnCl_2$-$[(C_6H_{11})_3P]$
   $PdCl_2$-$SnCl_2$-$[(C_6H_5)_2(p-CH_3C_6H_4)P]$
   $PdCl_2$-$GeCl_2$-$[(C_6H_5)_3P]$, and
   $PdCl_2$-$SnCl_2$-$[(C_6H_5)_3P]$
   and at least a molar equivalent of hydroxylated co-reactant containing 1 to 12 carbon atoms, to make a reaction mixture;
   b. pressurizing said reaction mixture to superatmospheric pressures ranging from about 100 to 3000 psig with sufficient carbon monoxide to satisfy the stoichiometry of the unsaturated ester reaction;
   c. heating said pressurized reaction mixture to at least about 20° C to 120° C, until insertion of carbon monoxide into the carbon-halogen bond of the alpha-vinylic monohalide takes place with displacement of halogen to produce said alpha-unsaturated alphatic esters of carboxylic acids, and
   d. isolating said alpha-unsaturated acid ester contained therein.

2. The process of claim 1 wherein the three component palladium catalyst is formed in situ in the presence of inert solvent.

3. The process of claim 2 wherein at least a stoichiometric quantity of Group VB donor ligand is present in the reaction mixture.

4. The process of claim 2 wherein the three component palladium catalyst is added to the reaction mixture preformed.

5. A process for converting unsaturated aliphatic allylic monohalides to Beta-unsaturated aliphatic esters of carboxylic acids in good yield and with good selectivity by a process of:
   a. admixing each mole of unsaturated aliphatic allylic monohalide to be converted to said Beta-ester, with at least a catalytic amount of a homogeneous palladium catalyst consisting of at least three components, a palladium halide, complexed with at least a stoichiometric quantity of a Group VB donor ligand, and in combination with a Group IVB metal halide co-catalyst, said catalyst being selected from the group consisting of:
   $PdCl_2$-$SnCl_2$-$[(p-CH_3O.C_6H_4)P]$
   $PdCl_2$-$SnCl_2$-$[(p-Cl.C_6H_4)_3P]$
   $PdCl_2$-$SnCl_2$-$[(CH_3)_2C_6H_5P]$
   $PdCl_2$-$SnCl_2$-$[(C_6H_{11})_3P]$
   $PdCl_2$-$SnCl_2$-$[(C_6H_5)_2(p-CH_3C_6H_4)P]$
   $PdCl_2$-$GeCl_2$-$[(C_6H_5)_3P]$, and
   $PdCl_2$-$SnCl_2$-$[(C_6H_5)_3P]$
   and at least a molar equivalent of hydroxylated co-reactant containing 1 to 12 carbon atoms, to make a reaction mixture;
   b. pressurizing said reaction mixture to superatmospheric pressures ranging from about 100 to 3000 psig with sufficient carbon monoxide to satisfy the stoichiometry of the unsaturated ester reaction;
   c. heating said pressurized reaction mixture to at least about 20° to 120° C, until insertion of carbon monoxide into the carbon halogen bond of the allylic monohalide takes place with displacement of halogen to produce said Beta-unsaturated alphatic esters of carboxylic acids, and
   d. Isolating said Beta-unsaturated acid ester contained therein.

6. The process of claim 5 wherein the three component catalyst is formed in situ in the presence of inert solvent.

7. The process of claim 5 wherein the three component catalyst is added to the reaction mixture preformed.

8. A process for converting vinyl halides to acrylate esters of the structure:

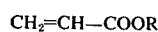

wherein R is an alkyl radical containing 1 to 12 carbon atoms, in good yield, and relatively free from halide contaminants by the process of:

a. admixing each mole of vinyl halide to be converted to acrylate esters with from 1 to 10 moles of alkanols containing 1 to 12 carbon atoms, in the presence of at least 1 molar equivalent of carbon monoxide, under superatmospheric pressures ranging from 500 psig to 2000 psig, with a catalyst consisting of from 0.005 to 0.02 molar equivalents of bis(triphenylphosphine)palladium(II) chloride, with from 0.025 to 0.20 molar equivalents of tin(II) chloride and 0.005 to 0.20 molar equivalents of triphenylphosphine, in the presence of sufficient inert solvent to disperse the components of the admixture, in a non-oxidizing atmosphere to form a reaction mixture;

b. heating said pressurized reaction mixture between about 80° C to 120° C until conversion of the vinyl halide to said acrylate esters takes place, and c. isolating said acrylate esters contained therein.

9. The process of claim 8 wherein the vinyl halide is vinyl chloride.

10. The process of claim 8 wherein the vinyl halide is vinyl bromide.

11. The process of claim 8 wherein the alkanol is methanol.

12. A process for converting allyl halides to vinylacetate esters of the structure:

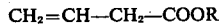

wherein R is an alkyl radical containing 1 to 12 carbon atoms, in good yield, and relatively free from halide contaminants by the process of:

a. admixing each mole of allyl halide to be converted to vinylacetate ester with from 1 to 10 moles of alkanol containing 1 to 12 carbon atoms, in the presence of at least 1 molar equivalent of carbon monoxide, under superatmospheric pressures ranging from 500 psig to 3000 psig, with a catalyst consisting of from 0.005 to 0.02 molar equivalents of bis-(triphenylphosphine)-palladium (II) chloride, with from 0.025 to 0.20 molar equivalents of tin(II) chloride, in the presence of sufficient inert solvent to disperse the components of the admixture, in a non-oxidizing atmosphere to form a reaction mixture;

b. heating said pressurized reaction mixture between about 80° to 120° C until conversion of the allyl halide to said vinylacetate ester takes place, and c. isolating said vinylacetate esters contained therein.

13. The process of claim 12 wherein the allyl halide is allyl chloride.

14. The process of claim 12 wherein the alkanol is methanol.

15. A process for converting aliphatic acetylene monohalides to Beta-unsaturated aliphatic esters of carboxylic acids in good yield and relatively uncontaminated with halogen-containing by-products by a process of:

a. admixing each mole of unsaturated acetylene aliphatic monohalide to be converted to said Beta unsaturated aliphatic ester, with at least a catalytic amount of a homogeneous noble metal catalyst consisting of at least three components, a palladium halide, complexed with at least a stoichiometric quantity of a Group VB donor ligand, and in combination with a stoichiometric excess of a Group IVB metal halide co-catalyst, said Beta-unsaturated aliphatic ester catalyst selected from the group consisting of:

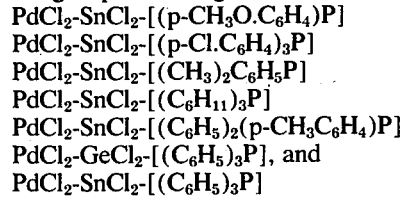

and at least a molar equivalent of hydroxylated co-reactant containing 1 to 12 carbon atoms, to make a reaction mixture;

b. pressurizing said reaction mixture to superatmospheric pressures ranging from about 100 to 3000 psig with sufficient carbon monoxide to satisfy the stoichiometry of the unsaturated ester reaction;

c. heating said pressurized reaction mixture to at least about 20° to 120° C, until insertion of carbon monoxide into the carbon halogen bond of the acetylene monohalide takes place with displacement of halogen to produce said Beta-unsaturated alphatic esters of carboxylic acids, and d. isolating said Beta unsaturated acid ester contained therein.

* * * * *